United States Patent
Brignac et al.

(10) Patent No.: US 9,019,364 B2
(45) Date of Patent: Apr. 28, 2015

(54) REMOTE VISUAL INSPECTION SYSTEM

(75) Inventors: Jacques L. Brignac, Simsbury, CT (US); Robert E. Lucas, Southbury, CT (US); George Rowland, Winsted, CT (US)

(73) Assignee: ALSTOM Technology Ltd, Baden (CH)

(*) Notice: Subject to any disclaimer, the term of this patent is extended or adjusted under 35 U.S.C. 154(b) by 314 days.

(21) Appl. No.: 13/550,928

(22) Filed: Jul. 17, 2012

(65) Prior Publication Data

US 2014/0022374 A1      Jan. 23, 2014

(51) Int. Cl.
*H04N 7/18* (2006.01)
*H04N 1/00* (2006.01)

(52) U.S. Cl.
CPC .................. *H04N 1/00095* (2013.01)

(58) Field of Classification Search
USPC .............. 348/82–85; 324/323, 344, 334; 73/152.01, 865.8; 250/256, 261, 265; 340/853.2, 856.3
See application file for complete search history.

(56) References Cited

U.S. PATENT DOCUMENTS

| | | | |
|---|---|---|---|
| 2,742,259 A | 4/1956 | Boucher | |
| 4,006,359 A | 2/1977 | Sullins et al. | |
| 4,108,004 A | 8/1978 | Murakami | |
| 4,616,258 A * | 10/1986 | Ono et al. | 348/84 |
| 5,359,898 A | 11/1994 | Latimer | |
| 5,454,267 A | 10/1995 | Moreau et al. | |
| 5,476,010 A | 12/1995 | Fleming et al. | |
| 5,549,004 A | 8/1996 | Nugent | |
| 5,652,617 A * | 7/1997 | Barbour | 348/85 |
| 6,002,993 A * | 12/1999 | Naito et al. | 702/154 |
| 6,271,670 B1 | 8/2001 | Caffey | |
| 6,282,964 B1 | 9/2001 | Hancock et al. | |
| 6,373,914 B1 | 4/2002 | Gill et al. | |
| 6,502,452 B1 | 1/2003 | Gill et al. | |
| 6,567,795 B2 | 5/2003 | Alouani et al. | |
| 6,683,641 B1 * | 1/2004 | MacCracken et al. | 348/82 |
| 6,748,808 B2 | 6/2004 | Lam et al. | |
| 6,799,466 B2 | 10/2004 | Chinn | |
| 6,889,783 B1 | 5/2005 | Moore et al. | |
| 6,920,792 B2 | 7/2005 | Flora et al. | |
| 7,201,055 B1 | 4/2007 | Bagley et al. | |

(Continued)

FOREIGN PATENT DOCUMENTS

| DE | 195 29 782 | 2/1997 |
|---|---|---|
| EP | 0 378 480 | 7/1990 |
| GB | 2015736 | 9/1979 |

(Continued)

OTHER PUBLICATIONS

Office action issued from Japanese Patent Office dated Jan. 13, 2015 for JP Application No. 2013-148607.

(Continued)

*Primary Examiner* — Victor Kostak

(57) ABSTRACT

A visual inspection system [100] includes a remote end [110] that is moved through a conduit [1] with a flexible pushrod [400]. The remote end [110] having at least one carriage assembly [130] with encoders [140] indicating a distance traveled within the conduit [1]. The visual inspection device [100] has a longitudinal camera [150] to identify view down the length of the conduit [1], but also has at least one transverse camera [160] adapted to visually inspect an inside surface [3] of the conduit [1]. Also, the transverse camera [160] may be used to inspect other conduits that connect to conduit [1].

13 Claims, 3 Drawing Sheets

(56) References Cited

U.S. PATENT DOCUMENTS

| | | |
|---|---|---|
| 7,587,942 B2 | 9/2009 | Smith et al. |
| 8,547,428 B1* | 10/2013 | Olsson et al. ............... 348/84 |
| 2003/0188589 A1 | 10/2003 | Harthorn et al. |
| 2004/0012672 A1* | 1/2004 | Shiota ............... 348/84 |
| 2004/0083829 A1 | 5/2004 | Chapman et al. |
| 2005/0034544 A1* | 2/2005 | Thornhill et al. ........... 73/865.8 |
| 2005/0104600 A1* | 5/2005 | Cotton ............... 324/519 |
| 2006/0164512 A1* | 7/2006 | Hinn ............... 348/84 |
| 2006/0290779 A1* | 12/2006 | Reverte et al. ............... 348/84 |
| 2008/0073495 A1* | 3/2008 | Heckendorn et al. ......... 250/253 |
| 2008/0098832 A1* | 5/2008 | Abbasi et al. ............... 73/865.9 |
| 2012/0169841 A1* | 7/2012 | Chemali et al. ............... 348/36 |
| 2013/0276558 A1* | 10/2013 | Lofstrom ............... 73/866.5 |

FOREIGN PATENT DOCUMENTS

| | | |
|---|---|---|
| GB | 1559469 | 1/1980 |
| JP | S60-125561 | 7/1985 |
| JP | S63-243808 | 10/1988 |
| JP | S64-54234 | 3/1989 |
| JP | H01-210852 | 8/1989 |
| JP | 2002-243649 | 8/2002 |
| JP | 2006-126022 | 5/2006 |
| JP | 3163271 | 9/2010 |
| KR | 10-2012-103869 | 9/2012 |

OTHER PUBLICATIONS

Office action issued from Canadian Patent Office dated Feb. 5, 2015 for CA Application No. 2,821,086.

* cited by examiner

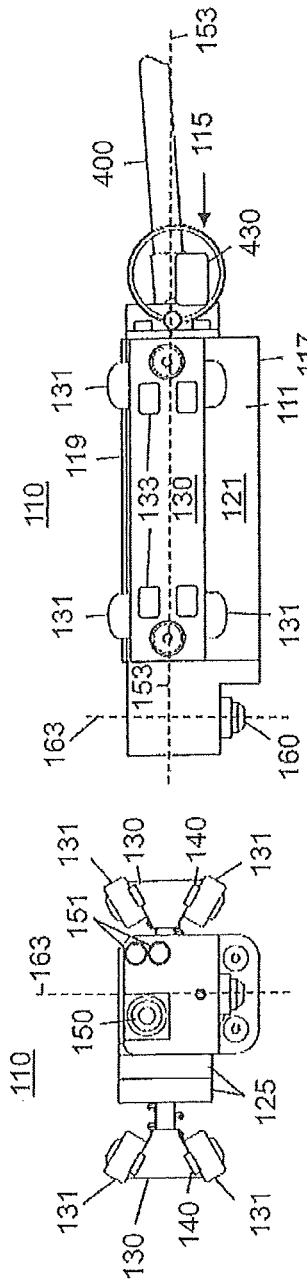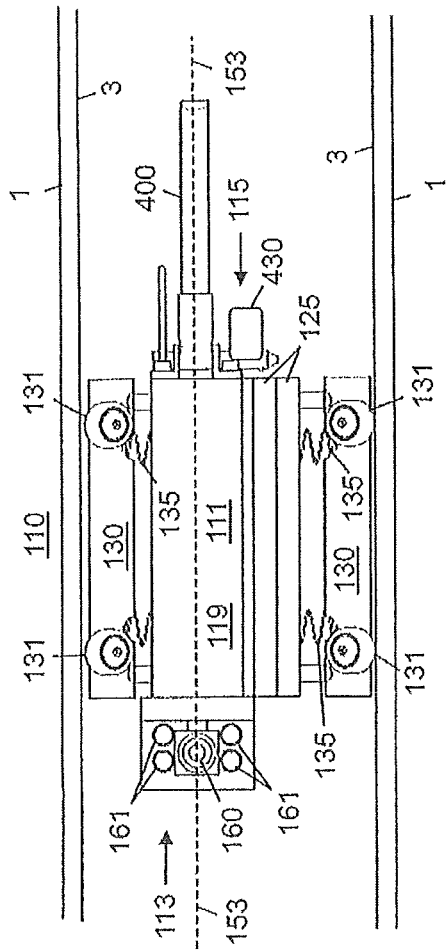

REMOTE VISUAL INSPECTION SYSTEM

BACKGROUND

The present disclosure generally relates to a system for a visually inspecting the inside of conduits, and more specifically, a system for visually inspecting the inside of pipes and boiler headers.

There are various kinds of equipment for inspecting the inside of pipes and other conduits that typically carry fluids. Since these conduits may corrode or develop cracks and other flaws, it is important to be able to inspect them. Visual inspection allows rapid identification of large sections of conduits to identify potential problem areas. It was determined that visual inspection of conduits is a quick way of identifying potential problems. These problem areas then can be inspected using additional inspection devices. Therefore, visual inspection is used as an initial inspection to detect generally where flaws may occur.

It is very important in some equipment, such as boilers that employ pipes that carry pressurized water and steam, to identify flaws before there they fail. A crack or flaw in one of these pressurized conduits can cause injury or fatality as well as significant damage to other equipment.

The inside of headers and associated waterwall pipes corrode and must be inspected. The headers are typically horizontal with vertical waterwall pipes extending from the horizontal header pipes. In a conduit that has a circular cross-section, all directions look similar, since there is no reference frame. Therefore, it is difficult to identify which direction the device is viewing solely from the camera image. This is especially true of symmetrical junctions, such as two pipes enter symmetrically from opposite sides of a conduit. Therefore, sometimes it is difficult to determine where the flaw is in a pipe.

Also, due to the geometry of some conduits, it is difficult to fully view the inside of various conduits. Even moveable cameras have a limit to their range of motion and it is difficult to view ahead of and to the sides of a device.

Currently, there is a need for a more versatile visual inspection device that can easily locate and identify problem areas inside of pipes.

BRIEF SUMMARY

The present invention may be embodied as a remote visual inspection system for visually inspecting an inside surface of an elongated conduit, having:
 a. A remote end comprising:
  i. a body having a front, rear, ventral side, dorsal side, and two lateral sides;
  ii. at least one carriage assembly extending from at least one of the later sides of the body for engaging said inside surface of said conduit;
  iii. a longitudinal camera on the front of the body, aimed to view ahead of the front of the body;
  iv. a transverse camera on the ventral side of the body, positioned to view said inside surface of the conduit; and
  v. an encoder to measure a distance travelled inside the said conduit;
 b. a flexible pushrod attached to the remote end, allowing the remote end to be moved along said conduit; and
 c. a control unit adapted receive, process, archive and analyze images from the remote end, as well as control the visual inspection system; and
 d. cabling connecting the remote end with the control unit.

The present invention may also be embodied as a method of visually inspecting an inside surface of a remote conduit, comprising the steps of:
 a. providing a remote end that has at least one sprung carriage assembly that rides along said inside surface stabilizing the remote end,
 b. measuring location within the conduit;
 c. acquiring longitudinal images of inside of the conduit at various locations within the conduit;
 d. acquiring transverse images of the inside of the conduit at various locations within the conduit;
 e. relating at least one of the longitudinal image or the transverse images of the inside of the conduit to their respective locations; and
 f. displaying at least one of the longitudinal and transverse images for given locations within the conduit.

The disclosure may be understood more readily by reference to the following detailed description of the various features of the disclosure and the examples included therein.

BRIEF DESCRIPTION OF THE DRAWINGS

Referring now to the figures wherein the like elements are numbered alike:

FIG. 2 is an end-on elevational view from the front of the visual inspection system of FIG. 1, according to one embodiment of the invention.

FIG. 3 is side elevational view of the visual inspection system of FIGS. 1 and 2 according to one embodiment of the invention.

FIG. 4 is plan view of the ventral side of the visual inspection system of FIGS. 1-3 according to one embodiment of the invention.

DETAILED DESCRIPTION

Theory

Figure 1:
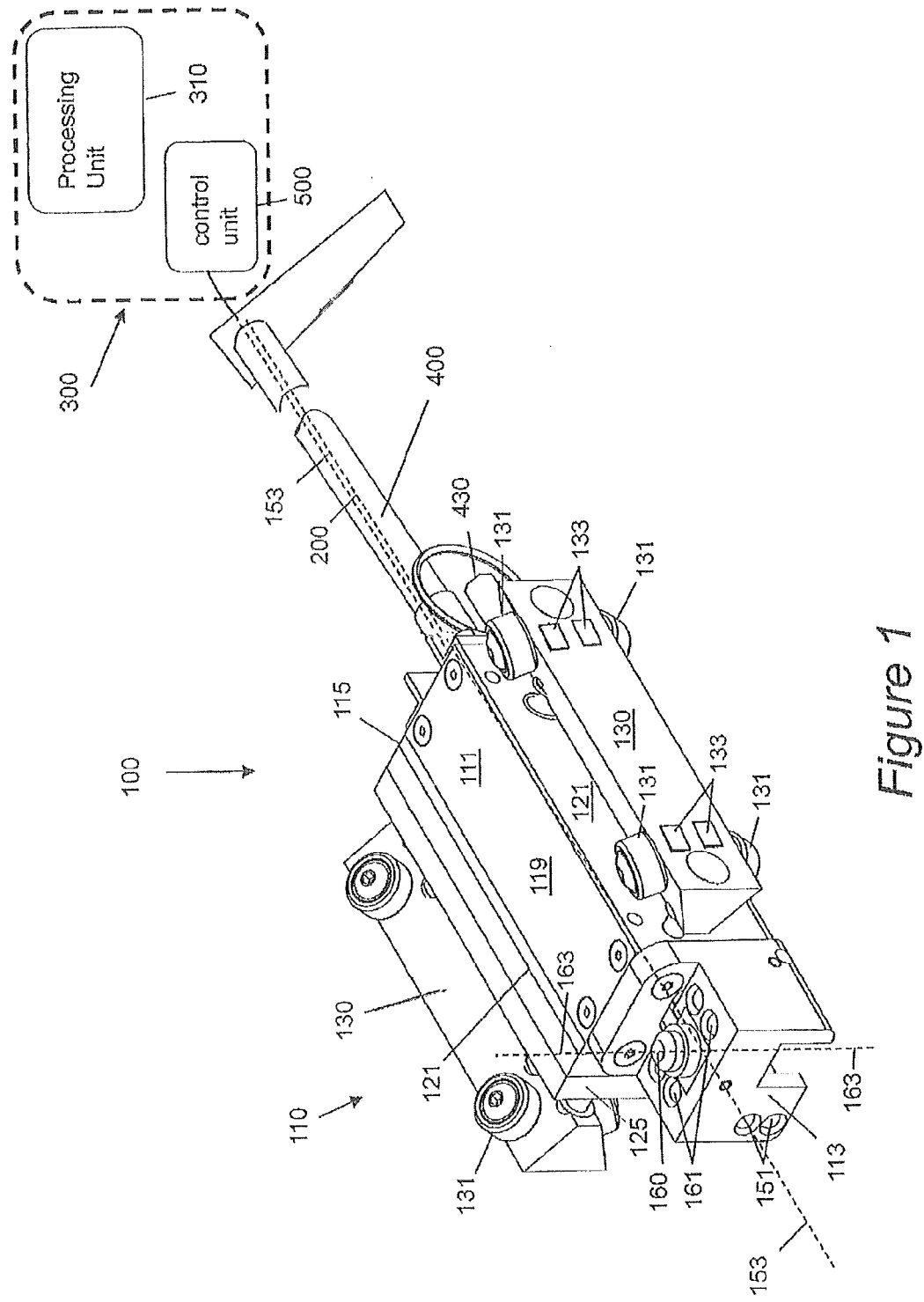
FIG. 1 is a perspective view of a visual inspection system according to one embodiment of the invention.

When visually inspecting the inside of a conduit, it is difficult to identify the location that a remote camera is viewing, when viewing a display. This is especially difficult when the remote camera is in a symmetrical conduit without a reference frame. Typically, the remote camera provides a view along a longitudinal length of the remote device having the remote camera, down the conduit in which it is travelling. The visual image not only is used for generally inspecting the conduit, it is useful in determining the progress along the conduit. It can be used to view obstructions, blockage and narrowing of the conduit due to debris, corrosion or buildup of foreign materials.

If a second conduit meets the first at a 90 degree angle, then the camera must be able to move, or otherwise provide and image at 90 degrees away from the original viewing angle to view down the length of the second conduit.

If the camera is angled 90 degrees from its longitudinal direction, (considered a transverse direction), such as to inspect a conduit extending perpendicularly from the conduit in which the remote device is traveling, the remote camera can no longer provide an image of the longitudinal direction along the direction of travel along the conduit, it cannot indicate any potential obstructions, etc.

Also, it is important to determine the orientation of the remote device, and have a means to adjust the orientation of the device.

This present invention relates to certain new and useful improvements in a visual inspection system that can quickly and accurately identify locations of flaws or defects inside conduits being inspected. It can also visually inspect conduits connecting to the conduit in which it is traveling and adjust its orientation to view various locations within these conduits.

Referring now to FIGS. 1-4, a visual inspection system 100 is shown that is designed for visually inspecting an inside surface of an elongated conduit such as a header or conduit 1.

It has a remote section 110 that has a body 111 having a front 113, rear 115, dorsal side 117, a ventral side 119 and two lateral sides 121. A longitudinal axis runs through the length of the body 111. A transverse axis 163 passes through the dorsal side 117 and the ventral side 119.

There is at least one carriage assembly 130 extending from at least one of the sides 121 of the body 111 for engaging said inside surface of said conduit. Preferably, wheels 131 extend from the carriage assembly 130 and are angled to roll along the inside surface 3 of the conduit 1.

An encoder 140 is coupled to the wheels 131 causing the encoder to determine how far along the conduit 1 that the wheels 131 have traveled. This information is passed through cabling 200 to a base unit 300 that calculates the instantaneous position of the remote section 110 along the conduit 1.

A longitudinal camera 150 is attached to the front of the body 111 and is oriented to view in a direction generally parallel to a longitudinal axis 150, down the length of the conduit 1. It is aimed to view ahead of the front 113 of the body 111. This is designed to look for obstructions ahead of the remote section 110, and to provide a visual image of the conduit ahead of the remote end 110.

A transverse camera 160 is attached to a ventral side 119, positioned to view generally in a direction generally along a transverse axis to view an area adjacent the ventral side 119 of the body 111.

A flexible pushrod 400 is attached to the remote section 110, for pushing/pulling the remote section 110 along the inside of the conduit 1.

The base 300 employs, among other components, a processing unit 310 adapted receive, process, archive and analyze images from the cameras 150, 160 of the remote section 110 inside of the conduit 1.

The base 300 also has a control unit 500 that is coupled to the remote section 110. The control unit can control the camera settings of longitudinal and transverse cameras 150, 160, and can also control actuators, such as zoom, focus as well as positioning devices to look in different directions. Control unit 500 may also control operation of lights, such as longitudinal LEDs 151 aimed to light an area viewed by the longitudinal camera 150. Similarly, transverse LEDs 161 are positioned to light an area viewed by the transverse camera 160.

FIG. 2 is an end-on elevational view from the front of the visual inspection system of FIG. 1, according to one embodiment of the invention.

Here the longitudinal camera 150 and the longitudinal light sources 151 are visible. The conduit 1 is not shown in this view; however, the wheels 131 are shown on the carriage assemblies 130 as they would appear as the wheels 131 ride along the inside surface of the conduit. The carriage assemblies have springs 135 or other urging devices that allow the carriages 130 to extend out to the inner surface to stabilize the remote end 110. This allows the remote end 110 to fit into various sized conduits 1, and remain stable minimizing movement of the image. This allows it to acquire steady visual images, with little shaking that are easier to analyze.

FIG. 3 is side elevational view of the visual inspection system of FIGS. 1 and 2 according to one embodiment of the invention. Here the carriage assembly 130 is visible. Also, transverse camera 160 is shown aimed along the transverse axis 163.

FIG. 4 is plan view of the ventral side of the visual inspection system of FIGS. 1-3 according to one embodiment of the invention. In this embodiment, springs 135 are used as urging devices pressing the carriage assemblies 130 and wheels 131 against the inside surface 3 or conduit 1.

Figure 5:
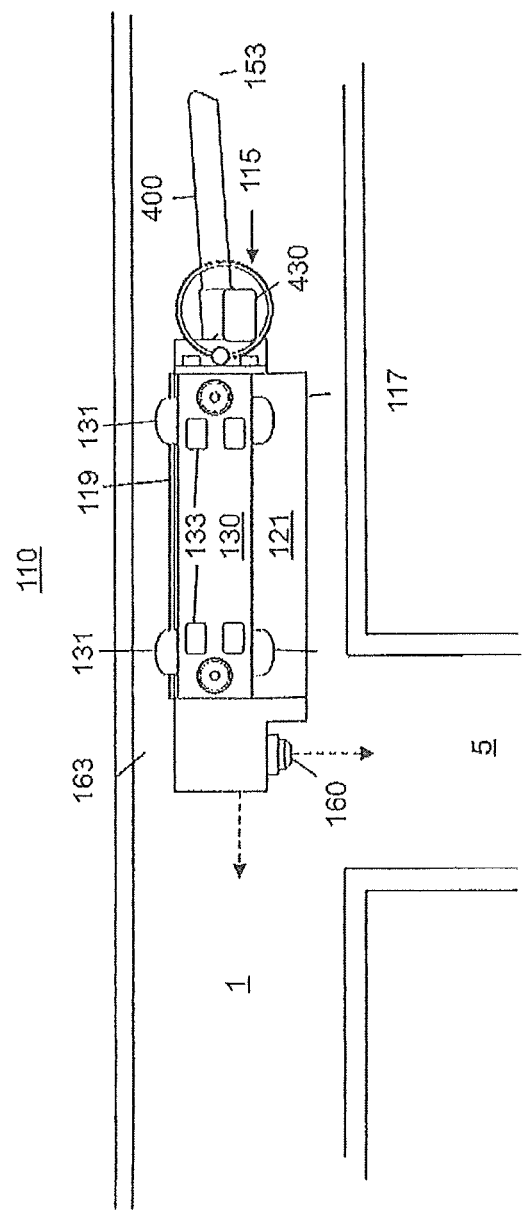
FIG. 5 is elevational view of the visual inspection system of FIGS. 1-4, as it would appear in use inspecting two intersecting conduits.

FIG. 5 is elevational view of the visual inspection system of FIGS. 1-4, as it would appear in use inspecting two intersecting conduits.

FIG. 5 shows a conduit 1 that intersects with another conduit 5 at a right angle. This is similar to the geometry of a horizontal steam header intersecting with downcomer tubes. This requires inspection and maintenance. The present invention is uniquely designed to inspect conduit 1 (the steam header) while also it can visually inspect conduit 5 (the down corner). It can do so while acquiring an image ahead in front of the remote end 110, to verify that there are no obstructions in conduit 1.

Alternative Embodiments

In an alternative embodiment of the system, slide pads 133 are used in addition to or instead of wheels 131. These slide pads are made of a low friction material, such as Teflon or nylon that slide along the inner surface of the conduit 1.

In another alternative embodiment of the present invention, conventional water spraying nozzle and/or wiper devices may be employed to clean off the lenses.

In still another embodiment of the present invention, a motor 430 may be employed that can rotate the remote end 110 with respect to the pushrod 400 to change the orientation of the remote end 110.

Advantageously, the present invention overcomes the problems noted in the prior art.

Unless otherwise specified, all ranges disclosed herein are inclusive and combinable at the end points and all intermediate points therein. The terms "first," "second," and the like, herein do not denote any order, quantity, or importance, but rather are used to distinguish one element from another. The terms "a" and "an" herein do not denote a limitation of quantity, but rather denote the presence of at least one of the referenced item. All numerals modified by "about" are inclusive of the precise numeric value unless otherwise specified.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A remote visual inspection system for visually inspecting an inside surface of an elongated conduit, comprising:
   a. a remote end comprising
      i. a body having a front, rear, ventral side, dorsal side, and two lateral sides;
      ii. at least one carriage assembly extending from at least one of the lateral sides of the body for engaging said inside surface of said conduit;

iii. a longitudinal camera on the front of the body, aimed to view ahead of the front of the body;
iv. a transverse camera on the ventral side of the body, positioned to view said inside surface of the conduit; and
v. an encoder to measure a distance traveled inside the said conduit;

b. a flexible pushrod attached to the remote end, allowing the remote end to be moved in rotation along said conduit; and c. a control unit adapted receive, process, archive and analyze images from the remote end, as well as control the visual inspection system; and d. cabling connecting the remote end with the control unit.

2. The remote visual inspection system of claim 1, further comprising:
at least one transverse light source positioned to light said inside surface of the conduit.

3. The remote visual inspection system of claim 1, further comprising:
at least one longitudinal light source positioned to light an area in front of the body.

4. The remote visual inspection system of claim 1, further comprising:
an orientation sensing device for identifying the orientation of the remote end relative to a vertical direction.

5. The remote visual inspection system of claim 1, wherein the pushrod further comprises:
a device for applying rotational force upon the pushrod thereby rotating the remote end relative to the conduit.

6. The remote visual inspection system of claim 1, wherein the longitudinal camera and the transverse camera provide images to the control unit that creates simultaneous views of both a longitudinal direction and a transverse direction within the conduit.

7. The remote visual inspection system of claim 1 further comprising:
an orientation sensing device that determines an orientation of the remote end relative to a vertical direction and provides the information to the control unit.

8. The remote visual inspection system of claim 1, further comprising:
an orientation adjustment device capable of rotating the remote end to adjust the remote end's orientation relative to a vertical direction.

9. The remote visual inspection system of claim 8, wherein the orientation adjustment device is a motor affixed to the pushrod capable of changing the orientation of the remote end with respect to the pushrod.

10. A method of visually inspecting an inside surface of a conduit, comprising the steps of:
a. providing a remote end that has at least one sprung carriage assembly that rides along said inside surface stabilizing the remote end;
b. measuring location within the conduit;
c. acquiring longitudinal images of inside of the conduit at various locations within the conduit;
d. acquiring transverse images of the inside of the conduit at various locations within the conduit;
e. relating at least one of the longitudinal images or the transverse images of the inside of the conduit to its respective locations; and
f. displaying at least one of the longitudinal images and transverse images for given locations within the conduit.

11. The method of claim 10, further comprising the steps of:
a. acquiring orientation information of the remote end as it acquires longitudinal images;
b. relating the orientation with the acquired longitudinal images; and
c. adjusting the displayed longitudinal images to correct for the orientation of the remote end.

12. The method of claim 10, further comprising the steps of:
a. acquiring orientation information of the remote end as it acquires transverse images;
b. relating the orientation with the acquired transverse images; and
c. providing an indication of the orientation of the remote end of the displayed transverse images when the transverse images are displayed.

13. The method of claim 10, wherein the step of displaying comprises:
simultaneously displaying the longitudinal and transverse images for given locations within the conduit.

* * * * *